United States Patent [19]

Clerici et al.

[11] Patent Number: 4,824,976
[45] Date of Patent: Apr. 25, 1989

[54] PROCESS FOR THE EPOXIDATION OF OLEFINIC COMPOUNDS AND CATALYSTS USED THEREIN

[75] Inventors: Mario G. Clerici; Ugo Romano, both of Milan, Italy

[73] Assignees: Eniricerche, S.p.A.; Enichem Sintesi, S.p.A., both of Milan, Italy

[21] Appl. No.: 4,680

[22] Filed: Jan. 20, 1987

[30] Foreign Application Priority Data

Jan. 28, 1986 [IT] Italy ............................... 19207 A/86
Jan. 28, 1986 [IT] Italy ............................... 19209 A/86

[51] Int. Cl.⁴ ............................................ C07D 301/12
[52] U.S. Cl. ..................................................... 549/531
[58] Field of Search .......................................... 549/531

[56] References Cited

U.S. PATENT DOCUMENTS 3,923,843 12/1975 Wulff .................................... 549/529
4,021,454  5/1977 Wulff et al. ........................ 549/529
4,410,501 10/1983 Taramasso et al. ................. 502/202
4,666,692  5/1987 Taramasso et al. ................. 423/339

FOREIGN PATENT DOCUMENTS 100119  2/1984 European Pat. Off. .

OTHER PUBLICATIONS

R. A. Sheldon, Journal of Molecular Catalysis, vol. 7 (1980), pp. 107, 114–118.

Primary Examiner—Richard L. Raymond
Assistant Examiner—Raymond Covington
Attorney, Agent, or Firm—Hedman, Gibson, Costigan & Hoare

[57] ABSTRACT

A process for the epoxidation of olefinic compounds comprising reacting said compounds with hydrogen peroxide introduced as such or produced by substances under the reaction conditions, in the presence of synthetic zeolites containing titanium atoms corresponding to the general formula:

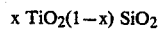

wherein x is in the range of from about 0.0001 to about 0.04, and optionally, in presence of one or more solvents, at a temperature in the range of from about 0° to about 150° C. and at a pressure of from about 1 to about 100 atm. The synthetic zeolites are treated with alkaline substances before and/or during their use in the reaction, or alternatively the synthetic zeolites are acid neutralized with a compound such as X-Si-(R)₃ where X is selected from Cl, Br, I,

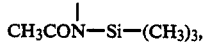

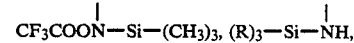

and an imidazolyl group wherein R is selected from an alkyl, aryl or alkylaryl group.

16 Claims, No Drawings

PROCESS FOR THE EPOXIDATION OF OLEFINIC COMPOUNDS AND CATALYSTS USED THEREIN

FIELD OF THE INVENTION

The present invention is directed to a process for the epoxidation of olefinic compounds with hydrogen peroxide introduced as such or produced by substances under the reaction conditions, in presence of synthetic zeolite containing titanium atoms, wherein the synthetic zeolites are neutralized as to their acidity.

BACKGROUND OF THE INVENTION

European Patent Application No. 100119 discloses a process for the epoxidation of olefinic compounds, starting from olefins and hydrogen peroxide or substances which can produce hydrogen peroxide under the reaction conditions, wherein the catalyst is a synthetic zeolite containing titanium atoms (titaniumsilicalite) corresponding to the general formula:

$$TiO_2 \cdot (1-x)SiO_2$$

wherein x is in the range of from 0.0001 to 0.04. The catalyst is chosen from among catalyst compositions having the following molar ratios of reactants:

| Molar Ratios of Reactants | | Preferred Molar Ratios |
| --- | --- | --- |
| $SiO_2/TiO_2$ | 5–200 | 35–65 |
| $OH^-/SiO_2$ | 0.1–1.0 | 0.3–0.6 |
| $H_2O/SiO_2$ | 20–200 | 60–100 |
| $Me/SiO_2$ | 0.0–0.5 | 0 |
| $RN^+/SiO_2$ | 0.1–2.0 | 0.4–1.0 | wherein $R^+$ represents an organic nitrogen cation derived from the organic base utilized for the preparation of titanium-silicalite (TS-1). Me is an alkaline ion, preferably chosen from among Na or K.

The final TS-1 product is a composition having the formula $x\,TiO_2 \cdot (1-x)SiO_2$ wherein x is in the range of from 0.0001 to 0.04, preferably from 0.01 to 0.025. TS-1 is silicalite-type product wherein titanium atoms vicariate the silicon atoms. A further and more precise identification of the titanium-silicalite which is used as a catalyst is set forth in said European patent application and in Belgian Pat. No. 886812.

The titanium-silicalite catalyst may be utilized in the epoxidation reaction as a dust or preferably in the form of granules having a particle size of from 5 to 1000 μm wherein the granules are made of zeolitic crystals bound by a suitable inorganic binder, preferably oligomeric silica.

It has been observed that in the synthesis of epoxide compounds derived from olefins and hydrogen peroxide with said catalysts in a protic medium (such as water, alcohol and mixtures thereof), selectivity of the desired epoxide is generally very high. Yet some amount of by-products from hydrolysis is always present, especially when working at high temperatures. This results in increased costs because of the lower yield of the epoxide and because of the need to separate the by-products from the reaction.

It has surprisingly been found that it is possible to significantly reduce the amount of the aforesaid undesirable by-products by treating the catalyst prior to the reaction or during the reaction with suitable acid neutralizing agents to neutralize acid groups which are on the catalyst surface. The catalyst can also be treated with a substance which can neutralize catalyst acidity using an inert group bound to a polar group which is easily displaced by reaction with SiOH.

The acidity of non-treated titanium-silicalite is already very low which is due to the presence of some SiOH groups, especially on the outer surface of the crystals or in the lattice defects. However, the presence of even a small number of acid groups results in the production of unacceptable amounts of by-products due to the hydrolysis reaction described above.

SUMMARY OF THE INVENTION

The process of the epoxidation of olefinic compounds in accordance with the present invention comprises reacting in a reaction zone one or more olefinic compounds with hydrogen peroxide or substances which produce hydrogen peroxide under the reaction conditions, in presence of a catalyst comprised of a synthetic zeolite (titanium-silicalite), wherein the catalyst is, prior to the epoxidation reaction, neutralized as to its acidity by a compound of the formula $X-Si-(R)_3$ wherein X is selected from Cl, Br, I, $$CH_3CO\overset{|}{N}-Si-(CH_3)_3,$$

$$CF_3CO\overset{|}{O}N-Si-(CH_3)_3, \quad (R)_3-Si-\overset{|}{N}H,$$

and an imidazolyl group, wherein R is an alkyl, aryl or alklaryl group wherein the alkyl group has from 1 to 4 carbon atoms.

Catalyst neutralization may also be accomplished before and/or during the reaction, with basic substances which are water soluble. Such basic substances may be chosen from among strong bases, such as NaOH, KOH, and weak bases such as $NH_4OH$, $Na_2CO_3$, $NaHCO_3$, $Na_2HPO_4$ and analogous potassium and lithium salts including $K_2CO_3$, $Li_2CO_3$, $KHCO_3$, $LiHCO_3$ and $K_2HPO_4$, alkali and/or alkaline-earth salts of carboxylic acids having from 1 to 10 carbon atoms and alkal and/or alkaline earth alcoholates, having from 1 to 10 carbon atoms.

In a batchwise epoxidation reaction, neutralization of the catalyst with basic substances, which are water soluble, is carried out by forming a slurry of the catalyst in a diluted solution of the neutralizing agent chosen among those mentioned above and stirring the slurry at a temperature of from about room temperature to about 100° C. for a few minutes. The catalyst is then removed and thoroughly washed to completely remove excess base. After drying, the catalyst is utilized for the epoxidation of the olefin, with surprisingly high selectivity to epoxide. In the event the epoxidation reaction is performed in a continuous flow (fixed bed reactor, CSTR reactor, i.e., continuous flow stirred tank reactor), it is sufficient to add to the hydrogen peroxide feed from about 0.0001 to about 0.1% by weight of a neutralizing agent which is soluble in the medium and weakly basic, (e.g. $CH_3COONa$, $Na_2HPO_4$, $Na_2CO_3$ and the like) in order to prevent deterioration of the catalyst over time. In this way, it is possible to prevent idenfinitely the catalyst from initiating the undesirable hydrolysis by product formation reaction. The amount of the neutralizing agent which is employed depends on the nature of the reaction medium, the space velocity, and the temperature.

Alternatively, neutralization of the catalyst is conducted by reacting the compounds of the general formula (X—Si—(R)$_3$) with the titanium-silicalite.

The reaction may be carried out in an inert solvent such as acetonitrile, chloroform, pyridine and dioxane and the like with or without an organic base such as pyridine or at least one tertiary amine. In accordance with this procedure, it is possible to transform all of the SiOH groups present on the surface of the titanium-silicalite, to SI—O—Si—(R)$_3$ groups which are chemically inert to hydrolysis of the epoxy ring.

The epoxidation reaction between the olefin and hydrogen peroxide is performed at a temperature of from about 0° to about 150° C. and at a pressure of from about 1 to about 100 atm with or without the presence of one or more solvents.

The epoxidation reaction may be performed in batch or in a continuous flow on a fixed bed, or in a CSTR reactor in a monophase or biphase system.

The catalyst is stable under the reaction conditions and may be completely recovered and reused. Examples of the solvents which can be used include polar compounds such as alcohols, ketones, esters, ethers, glycols, with the number of carbon atoms not too high, preferably less than or equal to 6 carbon atoms. Preferred examples of the alcohols are methanol and ter-butanol. A preferred example of a ketone is acetone.

The olefinic compounds that may be epoxidized according to the present invention include compounds having the general formula:

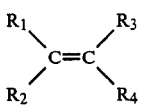

wherein R$_1$, R$_2$, R$_3$, and R$_4$ may be the same or different and are selected from H and an alkyl, alkylaryl, cycloalkyl and alkylcycloalkyl group, wherein the alkyl group has been 1 to 20 carbon atoms, the alkylaryl group has from 7 to 20 carbon atoms, the cycloalkyl group has from 6 to 10 carbon atoms and the alkylcycloalkyl group has from 7 to 20 carbon atoms. The R$_1$, R$_2$, R$_3$ and R$_4$ groups may be coupled together to form saturated or unsaturated rings (e.g., R$_1$, R$_2$ may be coupled together and/or R$_3$ and R$_4$ may be coupled together).

The R$_1$, R$_2$, R$_3$, and R$_4$ groups described above may be substituted with at least one substituent selected from halogen (preferably Cl, Br and I), nitro, sulfonic, carbony, hydroxyl, carboxylic and ether groups. By way of example, the olefins that may be epoxidized in accordance with the present invention are e.g., ethylene, propylene, allyl chloride, butene-2, butene-1, octene-1, 1-tridecene, mesityl oxide, isoprene, cyclooctene and cyclohexene and the like.

It is desirable to conduct the epoxidation reaction at a pressure higher than atmospheric pressure if gaseous olefins are used, in order to make them soluble or liquid under the reaction conditions. Operating at temperatures higher than 0° C. influences the kinetics of the reaction although the reaction proceeds rapidly even at temperatures near 0° C.

The following examples are directed to particular embodiments of the present invention. It should be noted, however, that the examples are merely illustrative and are not meant to limit the invention as set forth in the claims forming part of the application.

EXAMPLE 1

1154 g of tetraethylorthosilicate were added under strong stirring to 1232 g of a 12% by weight tetrapropylammonium hydroxide solution and heated for one hour at 60° C. 5049 g of demineralized water were added to the heated solution and stirring was continued for another hour until a clear solution was obtained. 3000 g of titanium-silicalite was carefully slurried into the clear solution. The titanium-silicalite is prepared according to the method disclosed in European patent application No. 100119 incorporated herein by reference.

The resulting milky slurry was fed to a spray-dryer (Niro-Atomizer, disk-atomizer, inlet air temperature 300° C.; outlet air temperature 120° C., chamber diameter 1.5 m) obtaining dense microspheres having a means diameter of about 20 μm.

The atomized catalyst was put in a muffle and calcined for four hours at 550° C. 200 g of atomized titanium-silicalite thus prepared were slurried in 1 liter of distilled water containing 10 g of sodium acetate. The slurry was heated at reflux temperature for 10 minutes and then filtered. The aforementioned treatment was repeated a second time in the same way with the same reactant. The resulting product was filtered again and then washed many times with hot distilled water. Then the washed catalyst was dried in a stove and then in a muffle at 550° C.

EXAMPLE 2

150 g of titanium-silicate prepared in the same manner as in Example 1, were slurried in 500 ml of water containing 5 g of Na$_2$HPO$_4$. The slurry was heated at reflux temperature for 15 minutes. The heated slurry was filtered and the treatment was repeated a second time. Thereafter the resulting product was washed repeatedly as described in Example 1.

Similar dilute solutions using other bases may be employed in the same manner to prepare highly active and selective epoxidation catalysts.

EXAMPLE 3

195 g of distilled water, 280 g of methanol and 4.5 g of catalyst prepared as described in Example 1, were loaded into a one liter steel autoclave provided with a mechanical stirrer, a thermostatic system and means for maintaining constant pressure. 56 g of a 325% by weight hydrogen peroxide solution were loaded in a tank connected to the autoclave. After thermostating at 40° C. and pressurizing with propylene under stirring at 6 atm (constant during the entire reaction), hydrogen peroxide was added in a single step to the slurry in the autoclave. Samples were taken at set time intervals and analyzed.

Hydrogen peroxide was titrated by iodometry and the reaction products were analyzed by gas chromatography, utilizing a column filled with Poropak PS, 1.8 m long. The results are shown in Table 1.

EXAMPLE 4

The procedure of Example 3 was followed using the same quantities of reactants, except that 4.5 g of the titanium-silicalite atomized as such without treatment with a base was used to carry out epoxidation of propylene. The results are shown in Table 1. As shown in Table 1, the results obtained using titanium-silicalite, without treatment with a base were not as good as those obtained with the base treated catalyst.

TABLE 1

| t(min) | Example 3 | | | Example 4 | | |
|---|---|---|---|---|---|---|
| | H$_2$O$_2$ (M/Kg) | PO (M/Kg)* | Others (M/Kg)** | H$_2$O$_2$ (M/Kg) | PO (M/Kg)* | Others (M/Kg)** |
| 4' | 0.744 | 0.245 | 0.001 | 0.661 | 0.320 | 0.007 |
| 12' | 0.421 | 0.562 | 0.004 | 0.371 | 0.590 | 0.020 |
| 24' | 0.225 | 0.757 | 0.008 | 0.185 | 0.753 | 0.052 |
| 40' | 0.051 | 0.917 | 0.021 | 0.058 | 0.865 | 0.067 |

*PO = Propylene oxide.
**Propylene glycol, 1-methoxy-2-hydroxypropane, 2 methoxy-1-hydroxypropane.

EXAMPLE 5

450 g of methanol, 100 g of octene-1, 5 g of catalyst prepared as in Example 2 were loaded in a 1 liter autoclave, provided with a mechanical stirrer, thermostatic system and constant pressure control. 50 g of a 34% by weight solution of H$_2$O$_2$ were loaded in the tank connected to the autoclave. After thermostating at 45° C., under strong stirring, hydrogen peroxide was added to the mixture of the other reactants. Samples were drawn at regular time intervals and analyzed.

Hydrogen peroxide was determined through iodometry and the reaction products determined by gas liquid chromatography, after 1 hour of reaction time:

H$_2$O$_2$ Conversion: 88%
Octene Conversion: 49.2%
Selectivity to 1,2-epoxyoctane: 98%

EXAMPLE 6

400 g of methanol, 100 g of allyl chloride, 10 g of catalyst prepared as in Example 1, were put in an autoclave as in Example 5. 70 g of a 34% by weight solution of H$_2$O$_2$ were loaded into the tank. The reaction was carried out at 60° C. for 30 minutes. Hydrogen peroxide and allyl chloride conversion and selectivity to epichlorohydrin was measured in the same general manner described in Example 5.

H$_2$O$_2$ Conversion: 93%
Allyl Chloride Conversion: 49.7%
Selectivity to Epichlorohydrin: 97.5%

EXAMPLE 7

21 g of titanium-silicalite prepared in the same manner as in Example 1, calcined at 550° C. and cooled in a dry atmosphere, were slurried in a mixture of 20 cc of anhydrous pyridine, 9 cc of trimethylchlorosilane and 3 cc of hexamethyldisilazane. The slurry was kept under stirring at 50° C. for 2 hours. The solid was then filtered, washed twice with 10 cc of anhydrous pyridine, twice with 10 cc of acetonitrile, three times with 10 cc of water and then thoroughly dried in vacuo.

EXAMPLE 8

1154 g of tetraethylorthosilicate were added under strong stirring to 1232 g of a 12% by weight solution of tetrapropylammonium hydroxide and heated for 1 hour at 60° C. 5049 g of demineralized water were then added to the heated mixture and stirring was maintained for another hour to thereby obtain a clear solution. 3000 g of titanium-silicalite, prepared according to Example 1 were carefully slurried into the clear solution.

The resulting milky slurry was fed to a spraydryer (Niro Atomizer, disk atomizer; inlet air temperature 300° C.; outlet air temperature 120° C.; chamber diameter 1.5 m) obtaining dense microspheres having a mean diameter of about 20 μm.

The atomized catalyst was put in a muffle and calcined for four hours at 550° C. 12 g of the resulting titanium-silicalite thus prepared were treated at 80° C. with 6 cc of bis(trimethylsilyl)acetamide in 10 cc of anhydrous acetonitrile for 2 hours.

The thus obtained solid product was filtered, washed many times with hot acetonitrile, and then methanol. The washed product was dried in a stove at 100° C.

EXAMPLE 9

In a similar manner as described in Example 8, 10 g of titanium-silicalite was treated with 3 cc of hexamethyldisilazane in 10 cc of acetonitrile. After refluxing for 2 hours, the resulting product was filtered, washed many times with acetonitrile and finally washed three times with water. The washed product was then dryed in vacuo.

EXAMPLE 10

190 g of distilled water, 280 g of methanol and 4.5 g of titanium-silicalite were loaded into a 1 liter steel autoclave, provided with a mechanical stirrer, thermostatic system and constant pressure control. 52 g of a 34% by weight solution of hydrogen peroxide were loaded in a tank connected to the autoclave.

After thermostating at 40° C. and pressuring with propylene, under stirring, at a constant pressure of 6 atm, the entire amount of hydrogen peroxide was added in a single step to the contents of the autoclave. Samples were drawn at regular intervals and analyzed. Hydrogen peroxide was titrated by iodometry and the reaction products were analyzed by gas-liquid chromatography on a column filled with Poropak PS, 1.8 m long. The results are shown in Table 2.

EXAMPLE 11

A test was carried out in the same way and with the same reactants as those in Example 10, except that 4.5 g of titanium-silicalite treated in the same manner as Example 7 were loaded into the autoclave. The results are shown in Table 2. As shown in Table 2, the selectivity to the desired epoxide was significantly greater than the selectively using the untreated catalyst described in Example 10.

TABLE 2

| t(min) | Example 10 | | | Example 11 | | |
|---|---|---|---|---|---|---|
| | H$_2$O$_2$ (M/Kg) | PO (M/Kg)* | Others (M/Kg)** | H$_2$O$_2$ (M/Kg) | PO (M/Kg)* | Others (M/Kg)** |
| 4' | 0.660 | 0.320 | 0.006 | 0.783 | 0.208 | 0.002 |
| 12' | 0.371 | 0.590 | 0.020 | 0.481 | 0.503 | 0.008 |
| 24' | 0.186 | 0.753 | 0.054 | 0.235 | 0.747 | 0.009 |

TABLE 2-continued

| | Example 10 | | | Example 11 | | |
|---|---|---|---|---|---|---|
| t(min) | $H_2O_2$ (M/Kg) | PO (M/Kg)* | Others (M/Kg)** | $H_2O_2$ (M/Kg) | PO (M/Kg)* | Others (M/Kg)** |
| 40' | 0.058 | 0.865 | 0.067 | 0.089 | 0.881 | 0.020 |

*PO = Propylene oxide.
**Propylene glycol, 1-methoxy-2-hydroxypropane, 2 methoxy-1-hydroxypropane.

EXAMPLE 12

450 g of methanol, 100 g of octene-1, and 5 g of catalyst prepared as in Example 8, were loaded into a one liter autoclave, provided with a mechanical stirrer and a thermostatic system and a constant pressure control. 50 g of a 34% by weight solution of $H_2O_2$ were loaded in a tank connected to the autoclave. After thermostating at 45° C. under strong stirring, hydrogen peroxide was added to the mixture of the other reactants. Samples were drawn at regular intervals and analyzed.

Hydrogen peroxide was titrated by iodometry and the reaction products analyzed by gas-liquid chromatography after one hour.

$H_2O_2$ Conversion: 85%
Octene Conversion: 47.5%
Selectively to 1,2 epoxyoctane: 97.5%

EXAMPLE 13

The reaction was carried out in the same manner and with the same equipment as described in Example 12. 400 g of methanol, 100 g of allyl chloride, and 10 g of the catalyst prepared as in Example 9 were added to the autoclave. 70 g of a 34% by weight solution of $H_2O_2$ were loaded in the tank. The reaction was carried out at 60° C. for 30 minutes.

$H_2O_2$ Conversion: 94%
Allylchloride Conversion: 50.1%
Selectivity to Epichlorohydrin: 98%

We claim:

1. A process for the highly selective epoxidation of olefinic compounds comprising reacting in an aqueous solvent at least one olefinic compound with hydrogen peroxide or substances which produce hydrogen peroxide under the reaction conditions, in presence of a synthetic zeolite catalyst containing titanium atoms corresponding to the general formula x $TiO_2$. (1-x) $SiO_2$ wherein x is in the range of from 0.0001 to 0.04 and the titanium atoms replace at least a portion of the silicon atoms, and neutralizing the acidity of the catalyst with at least one neutralizing agent.

2. The process according to claim 1 wherein the step of neutralizing the acidity of the catalyst is conducted before, during or both before and during the epoxidation reaction.

3. The process according to claim 2 wherein the neutralizing agents are basic substances which are water soluble.

4. The process according to claim 3 wherein the basic substances are strong bases.

5. The process according to claim 4 wherein the strong bases are selected from NaOH and KOH.

6. The process according to claim 3 wherein the basic substances are weak bases.

7. The process according to claim 6 wherein the weak bases are selected from $NH_4OH$, $Na_2CO_3$, $NaHCO_3$, $Na_2HPO_4$ analogous potassium and lithium salts, alkali metal salts and alkaline earth metal salts of carboxylic acids having from 1 to 10 carbon atoms and alkali metal alcoholates and alkaline-earth metal alcoholates having from 1 to 10 carbon atoms and mixtures thereof.

8. The process according to claim 7 wherein the potassium and lithium salts are selected from $K_2CO_3$, $Li_2CO_3$, $KHCO_3$, $LiHCO_3$ and $K_2HPO_4$.

9. The process according to claim 2 wherein the step of acid neutralization occurs before the reaction, and the neutralizing agents are selected form compounds of the formula X—Si—(R)$_3$ wherein X is selected from Cl, Br, I, $$CH_3CON-Si-(CH_3)_3,$$

$$CF_3COON-Si-(CH_3)_3, (R)_3SiNH,$$

and an imidazolyl group, and R is selected from an alkyl, aryl and an alkylaryl group wherein the alkyl group has from 1 to 4 carbon atoms.

10. The process according to claim 9 wherein the step of acid neutralization occurs before the reaction by reacting the neutralizing agents with the catalyst in an inert solvent.

11. The process according to claim 10 wherein the inert solvent is selected from acetonitrile, chloroform, pyridine, dioxane or mixtures thereof, alone or in the presence of an organic base.

12. The process according to claim 11 wherein the organic base is selected from pyridine and at least one tertiary amine.

13. The process of claim 1 wherein the step of acid neutralization is conducted at a temperature of from about 0° C. to about 100° C.

14. The process of claim 3 further comprising conducting the epoxidation reaction in a continuous flow and adding from about 0.0001 to about 0.1% by weight of a neutralizing agent which is weakly basic and soluble in the reaction medium.

15. The process of claim 1 wherein the epoxidation reaction is conducted at a temperature of from about 0° C. to about 150° C. and at a pressure of from about 2 to about 100 atmospheres.

16. The process of claim 1 wherein the olefinic compounds are selected from compounds having the formula:

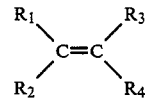

wherein $R_1$, $R_2$, $R_3$ and $R_4$ are the same or different and are selected from H and an alkyl, alkylaryl, cycloalkyl, alkylcycloalkyl group, wherein the alkyl group has from 1 to 20 carbon atoms, the alkylaryl group has from 7 to 20 carbon atoms, the cycloalkyl group has from 6 to 10 carbon atoms and the alkylcycloalkyl group has from 7 to 20 carbon atoms wherein the $R_1$, $R_2$, $R_3$ and $R_4$ are coupled together to form saturated or unsaturated rings or are not coupled together, in either coupled or not coupled state, the $R_1$, $R_2$, $R_3$ and $R_4$ are not substituted or are substituted with at least one substituent selected from halogen, nitro, sulfonic, carbonyl, hydroxyl, carboxylic and ether groups.

* * * * *